(12) United States Patent
Taylor et al.

(10) Patent No.: US 9,220,864 B2
(45) Date of Patent: Dec. 29, 2015

(54) ADSORBER REPLACEMENT NOTIFICATION FOR A PORTABLE GAS CONCENTRATOR

(71) Applicants: Brenton Taylor, Kenwood, CA (US); Peter Hansen, Santa Barbara, CA (US)

(72) Inventors: Brenton Taylor, Kenwood, CA (US); Peter Hansen, Santa Barbara, CA (US)

(73) Assignee: Inogen, Inc., Goleta, CA (US)

( * ) Notice: Subject to any disclaimer, the term of this patent is extended or adjusted under 35 U.S.C. 154(b) by 0 days.

(21) Appl. No.: 14/165,011

(22) Filed: Jan. 27, 2014

(65) Prior Publication Data

US 2014/0137741 A1 May 22, 2014

Related U.S. Application Data

(63) Continuation of application No. 13/449,138, filed on Apr. 17, 2012, now Pat. No. 8,702,841.

(51) Int. Cl.
*B01D 53/02* (2006.01)
*A61M 16/10* (2006.01)
*B01D 53/047* (2006.01)

(52) U.S. Cl.
CPC .............. *A61M 16/10* (2013.01); *A61M 16/101* (2014.02); *B01D 53/047* (2013.01); *B01D 53/0476* (2013.01); *A61M 2016/1025* (2013.01); *A61M 2205/18* (2013.01); *A61M 2205/502* (2013.01); *A61M 2205/583* (2013.01); *A61M 2205/707* (2013.01); *A61M 2205/7563* (2013.01); *B01D 2256/12* (2013.01); *B01D 2257/102* (2013.01); *B01D 2259/4533* (2013.01)

(58) Field of Classification Search
CPC .............. A61M 16/10; A61M 16/101; A61M 2016/1025; A61M 2205/18; A61M 2205/502; A61M 2205/583; A61M 2205/707; A61M 2205/7563; B01D 2256/12; B01D 2257/102
See application file for complete search history.

(56) References Cited

U.S. PATENT DOCUMENTS

| | | | | |
|---|---|---|---|---|
| 4,627,860 | A * | 12/1986 | Rowland | 96/111 |
| 6,035,851 | A * | 3/2000 | Wallen | 128/202.22 |
| 6,698,423 | B1 * | 3/2004 | Honkonen et al. | 128/201.21 |
| 2003/0189492 | A1 * | 10/2003 | Harvie | 340/573.1 |
| 2007/0056584 | A1 * | 3/2007 | Jagger et al. | 128/201.21 |
| 2011/0017062 | A1 * | 1/2011 | DiLeo et al. | 95/22 |

* cited by examiner

*Primary Examiner* — Christopher P Jones
(74) *Attorney, Agent, or Firm* — Mark Rodgers

(57) ABSTRACT

A portable oxygen concentrator designed for medical use where the usable life of the sieve beds, adsorbers, is monitored and communicated to the user or service provider through a user interface or a transmitted signal. The concentrator is designed so that the beds are easily replaced by the user or a field technician. Preferably PSA cycle operating parameters appropriate to the replaced beds can be easily reset if needed by the user or service provider.

7 Claims, 15 Drawing Sheets

Adsorbent Indicator Light

Adsorbent Life Remaining

Figure 10    Simple Sieve Bed Monitoring Algorithm for Remaining Sieve Bed Life

Monitored Parameters:
Oxygen Concentration, $[O_2]$
Product Pressure (PSI), $P_p$
Product Pressure (PSI), $P_{avg}$
Target Product Pressure (PSI), $P_T$
Column Balance (PSI), CB
Column Balance Adjustment, CBA
Cycle Frequency, CF
Cycle Frequency Adjustment, CFA
Operating Hours, OH
Fractional Duty Cycle, DC
Operating Temperature, $T_o$
Storage Temperatures, $T_s$ Remaining % Life = 100 − [10(95−$[O_2]$)]

Figure 11  Exemplary Sieve Bed Monitoring Algorithm
for Remaining Sieve Bed Life Monitored Parameters:
Oxygen Concentration, $[O_2]$
Product Pressure (PSI), $P_p$
Product Pressure (PSI), $P_{Avg}$
Target Product Pressure (PSI), $P_T$
Column Balance (PSI), CB
Column Balance Adjustment, CBA
Cycle Frequency, CF
Cycle Frequency Adjustment, CFA
Operating Hours, OH
Fractional Duty Cycle, DC
Operating Temperature, $T_o$
Storage Temperatures, $T_s$ Remaining % Life = $100 - [10(95-[O_2]) - 10(P_{Avg}-P_T) - 2*CFA - 2*CBA - OH/1000 - 1/DC]$ Figure 12    Alternative Sieve Bed Monitoring Algorithm
for Remaining Sieve Bed Life Monitored Parameters:
Oxygen Concentration, $[O_2]$
Product Pressure (PSI), $P_p$
Product Pressure (PSI), $P_{Avg}$
Target Product Pressure (PSI), $P_T$
Column Balance (PSI), CB
Column Balance Adjustment, CBA
Cycle Frequency, CF
Cycle Frequency Adjustment, CFA
Operating Hours, OH
Fractional Duty Cycle, DC
Operating Temperature, $T_o$
Storage Temperatures, $T_s$ Remaining % Life = $100 - [5(95-[O_2]) - 5(P_{Avg}-P_T) - 2*CFA - 2*CBA - OH/1000 - 2/DC - (T_o-35) - (T_s-25)]$ Figure 13    Alternative Sieve Bed Monitoring Algorithm #2 for Remaining Sieve Bed Life Monitored Parameters:
Product Pressure (PSI), $P_p$
Product Pressure (PSI), $P_{Avg}$
Target Product Pressure (PSI), $P_T$
Column Balance (PSI), CB
Column Balance Adjustment, CBA
Cycle Frequency, CF
Cycle Frequency Adjustment, CFA
Operating Hours, OH
Fractional Duty Cycle, DC
Operating Temperature, $T_o$
Storage Temperatures, $T_s$ Remaining % Life = 100 − 10($P_{Avg}$ − $P_T$) − 2*CFA − 2*CBA − OH/1000 − 1/DC]

Figure 14

Monitored Parameters:
Product Pressure (PSI), $P_p$
Product Pressure (PSI), $P_{Avg}$
Target Product Pressure (PSI), $P_T$
Column Balance (PSI), CB
Column Balance Adjustment, CBA
Cycle Frequency, CF
Cycle Frequency Adjustment, CFA
Operating Hours, OH
Fractional Duty Cycle, DC
Operating Temperature, $T_o$
Storage Temperatures, $T_s$ Remaining % Life = $100 - 5(P_{Avg} - P_T) - 2*CFA - 2*CBA - OH/1000 - 2/DC - (T_o - 35) - (T_s - 25)$]

| Parameter | Case 1 | Case 2 | Case 3 | Case 4 | Case 5 |
|---|---|---|---|---|---|
| [O2] | 94.8 | 93 | 92 | 90 | 85 |
| Pavg | 20 | 20.5 | 21 | 21 | 22.5 |
| PT | 20 | 20 | 20 | 20 | 20 |
| CFA | 0 | 0 | 2 | 8 | 16 |
| CBA | 0 | 1 | 1 | 2 | 2 |
| OH | 50 | 500 | 1500 | 5000 | 15000 |
| DC | 0.95 | 0.8 | 0.75 | 0.7 | 0.7 |
| To | 38 | 38 | 38 | 39 | 39 |
| Ts | 23 | 24 | 24 | 23 | 23 |
| Simple Algorithm | 98.00 | 80.00 | 70.00 | 50.00 | - |
| Alternative Algorithm | 98.70 | 89.25 | 78.17 | 58.57 | 12.57 |
| 2nd Alternative Algorithm | 97.70 | 87.25 | 76.17 | 56.57 | 10.57 |
| 3rd Alternative Algorithm | 98.90 | 91.25 | 81.17 | 63.57 | 22.57 |
| 4th Alternative Algorithm | 97.90 | 89.25 | 79.17 | 61.57 | 20.57 |

Figure 15

ADSORBER REPLACEMENT NOTIFICATION FOR A PORTABLE GAS CONCENTRATOR

RELATED APPLICATIONS

This application is a continuation of U.S. application Ser. No. 13/449,138, filed Apr. 17, 2012 and issued as U.S. Pat. No. 8,702,841

FEDERALLY SPONSORED RESEARCH

Not Applicable

SEQUENCE LISTING

Not Applicable

BACKGROUND OF THE INVENTION

The invention generally relates to gas concentrators, and more particularly relates to medical oxygen concentrators used by patients in the home care setting where predictive maintenance resulting in little or no unplanned downtime and minimized service cost is essential.

The application of oxygen concentrators for therapeutic use is known, and many variants of such devices exist. A particularly useful class of oxygen concentrators is designed to be portable, allowing users to move about and to travel for extended periods of time without the need to carry a supply of stored oxygen or to have any maintenance performed on their equipment by a service technician. These portable oxygen concentrators typically weigh 2 to 20 lbs and produce from 0.3 to 5.0 LPM of oxygen. Most of these portable concentrators are based on Pressure Swing Adsorption (PSA), Vacuum Pressure Swing Adsorption (VPSA), or Vacuum Swing Adsorption (VSA) designs which use one or more pumps to move air through selective adsorption beds at various adsorption and desoroption pressures. In a typical oxygen concentrator, the beds utilize a zeolite adsorbent to selectively adsorb nitrogen, resulting in pressurized, oxygen-rich product gas.

The main elements in a typical portable therapeutic oxygen concentrator are shown in FIG. 1. Air is draw in, and typically filtered, at air inlet 1 before being pressurized by compressor 2 to a pressure of 1.2 to 2.5 atmospheres. The pressurized air is directed by a valve arrangement through adsorbent beds 3. An exemplary adsorbent bed implementation, used in a concentrator design developed by the inventors, is two columns filled with a lithium exchanged zeolite adsorbent in the ratio of about 1 gram of adsorbent per 1-20 ml of oxygen produced. The pressurized air is directed through these adsorber vessels or columns in a series of steps which constitute a gas separation cycle, often a PSA cycle or some variation including vacuum instead of, or in conjunction with, compression yielding overall compression ratios of about 1.5:1 to 5.5:1. Although many different arrangements of adsorber vessels and gas separation cycles are possible, the result is that nitrogen is removed by the adsorbent material and the resulting oxygen rich gas is routed to a product gas storage device at 4. Some of the oxygen product gas can be routed back through the bed to flush out (purge) the adsorbed nitrogen to an exhaust 6. Generally multiple adsorbent beds, or columns in the exemplary device, are used so at least one bed may be used to make product while at least one other bed is being purged, ensuring a continuous flow of product gas. The purged gas is exhausted from the concentrator at the exhaust 6.

Such gas separation systems are known in the art, and it is appreciated that the gas flow control through the compressor and the adsorbent beds is complex and requires precise timing and control of parameters such as pressure, flow rate, and temperature to attain the desired oxygen concentration of 80% to 95% purity in the product gas stream. Accordingly, most modern concentrators also have a programmable controller 5, typically a microprocessor, to monitor and control the various operating parameters of the gas separation cycle. In particular, the controller controls the timing and operation of the various valves used to cycle the beds through feed, purge, and pressure equalization steps which make up the gas separation cycle. Also present in most portable concentrators is a conserver 7 which acts to ensure that oxygen rich gas is only delivered to a patient during inhalation. Thus, less product gas is delivered than by means of a continuous flow arrangement, thereby allowing for smaller, lighter concentrator designs. A pulse of oxygen rich air, called a bolus, is delivered in response to a detected breath via the conserver. Using a conserver in conjunction with a gas concentrator may reduce the amount of oxygen required to maintain patient oxygen saturation by a factor of about 2:1 to 9:1. A typical concentrator will also contain a user/data interface 8 including elements such as an LCD display, alarm LEDs, audible buzzers, and control buttons. In addition to the above subsystems, most portable oxygen concentrators contain a rechargeable battery and charging system to power the concentrator while away from an AC or DC power source. These battery systems are typically composed of lithium ion cells and can power the concentrator from 0.5-12 hours depending on the amount of oxygen required by the patient, device efficiency, and the capacity of the battery pack which may range from about 40 Watt-hours to 250 Watt-hours on systems with multiple battery packs.

To be practical and usable by a individual needing therapeutic oxygen, portable oxygen concentrators should be less than about 2100 cubic inches and preferably less than 600 cubic inches in total volume, less than about 20 pounds and preferably less than 8 pounds in weight, and produce less than about 45 decibels of audible noise, while retaining the capacity to produce a flow of product gas adequate to provide for a patient's oxygen needs, usually a flow rate prescribed by a medical practitioner in about the range of 1 LPM to 6 LPM. Further, a portable medical oxygen concentrator must work under varied environmental conditions such as 0° C. to 40° C. and 0%-95% relative humidity without costly or frequent service or maintenance requirements. Although fixed site PSA based concentrators have been available for many years, such fixed site units may weigh 30-50 pounds or more, be several cubic feet in volume, and produce sound levels greater than 45 dBA. Thus portable concentrators involve a significant amount of miniaturization, leading to smaller, more complex designs compared to stationary units. System size, weight, and complexity may lead to fewer mitigative options or design choices against contamination and other wear and tear effects that can lead to an unacceptably short maintenance interval.

One particular challenge of portable concentrator design is that the adsorbent beds must by necessity be small, yet capable of producing an adequate quantity of product gas. A portable oxygen concentrator might require oxygen production of greater than 3 ml of oxygen per gram of adsorbent in order to achieve an acceptable size of less than 600 cubic inches. Since the adsorbent beds are optimized for $O_2$ production per gram of adsorbent, any significant decrease in capacity of the beds over time can result in decreased product purity as the required $O_2$ production per gram of active adsorbent exceeds the limits of the adsorbent and PSA cycle operating parameters. One contributing factor that can lead to a decrease in bed capacity is the adsorption of impurities that do not completely desorb during normal process operation, leading to the accumulation and retention of impurities in the beds and therefore less active adsorbent than originally intended in the design. An example of such an impurity that reduces the adsorption capacity of many zeolites used in air separation is water. Some stationary concentrators utilize some means of removing water from the compressed gas before feeding the adsorbent beds, but most rely on an excess quantity of adsorbent to allow for contamination over time. Portable concentrators, by the nature of their application, are more likely to be exposed to a wide range of operating conditions including high humidity environments and/or rapid temperature changes that could result in the need for more frequent zeolite replacement. If water is present, either in the form of liquid (condensed out of the feed stream) or vapor, and enters the molecular sieve beds, the beds will irreversibly adsorb at least some of this water during each adsorption cycle. The energy of adsorption of water on lithium exchanged zeolites used in air separation is very high and not all water adsorbed during the adsorption steps in the process is desorbed during evacuation/purge of the beds under typical PSA cycle operating parameters. Therefore, complete removal of adsorbed water from zeolite beds usually entails applying some sort of energy to the beds, such as thermal, infrared, or microwave, and purging with a dry gas or applying a vacuum to the beds during the regeneration process. These regeneration processes are impractical in a portable concentrator due to high temperature or high power requirements as well as other design restraints, such as weight and size. As a result, the accumulation of adsorbed water over time results in a reduction in capacity of the beds, as fewer sites are available for nitrogen binding. Fewer binding sites in the adsorbent bed can result in a decrease in product purity over time as nitrogen passes through the sieve beds and dilutes the oxygen product gas, and shortens the service life of the concentrator. Many zeolites used in air separation, and in particular advanced adsorbents, particularly the high lithium containing low silica X type zeolite (LiLSX) used in portable concentrators, are hydrophilic in their activated state due to the interaction of the strong dipole moment of water molecules with the electric fields present in the LiLSX cages and can therefore be prone to this problem. In the effort to make more compact and efficient concentrators, PSA cycle frequencies can increase to rates approaching 10 cycles per minute and adsorbent productivity increases accordingly with advances in process and adsorbent technology to productivities exceeding 10.0 ml of oxygen per gram of adsorbent. The corresponding decrease in adsorbent inventory exacerbates the problem as the amount of gas processed per unit of adsorbent increases proportionally, (the bed size factor decreases) and the presence of impurities in the process gas can deactivate the adsorbents at a much faster rate than with conventional PSA processes, as described in U.S. Pat. Nos. 7,037,358 and 7,160,367, and U.S. application Ser. No. 13/066,716 which are incorporated by reference herein. The portable oxygen concentrator's duty cycle as well as operational and storage conditions can also impact the rate of adsorbent deactivation. When a concentrator is not running and no purge or evacuation cycling takes place, any moisture or other contaminants in a portion of a bed will diffuse into the rest of the bed, further decreasing the operational life of the bed.

It is therefore necessary to design portable oxygen concentrators such that zeolite contamination can be prevented or handled in a manner that avoids costly or frequent complex maintenance by a field technician or equipment provider. While the inventors have previously disclosed a system that achieves long sieve bed life by removing water prior to the feed gas contacting the zeolite in U.S. co-pending application Ser. No. 11/998,389, whose teachings are incorporated by reference, this approach adds size and cost to the system to achieve its resistance to zeolite contamination. It is therefore desirable to design a portable oxygen concentrator that minimizes size and weight as a function of oxygen output with commonly available LiLSX and LiX adsorbents from suppliers such as UOP, Zeochem, or Ceca. While eliminating water removal components such as membrane air dryers or pretreatment layers such as activated alumina or an NaX type zeolite will reduce the size and weight of the sieve beds it will also reduces the service life of the sieve bed. Oxygen equipment used for Long Term Oxygen Therapy (LTOT) is optimally deployed for 3-5 years without any service requirements. Any complex service requirement within that time interval simply adds to the overall cost of the equipment, which substantially reverses any cost benefit gained by removing a membrane air dryer or pretreatment layer. Further, allowing sieve bed contamination without prevention or service may lead to providing 82-87% purity oxygen instead of 87-95% pure oxygen to the patient. At this time, portable oxygen concentrator adoption will require smaller, lighter devices that do not require complex field service by a technician or equipment provider, but also minimize size and cost of the equipment. However, if water contamination is the main contributor to operational lifetime, changing out the beds and/or adsorbent can be a relatively simple, easy and fast process for a concentrator designed with simple maintenance by the patient or user in mind. For such a case, it is vital that a user know ahead of time when adsorbent change is required so that replacement adsorbers are available and reduced purity oxygen is not delivered to the patient.

A typical portable oxygen concentrator may contain an oxygen purity sensor that alerts the user or equipment provider when the output oxygen falls below a defined concentration. Such oxygen sensors may be fuel cells, ceramic, or ultrasonic in operating principle, but they ultimately are used for the same purpose, which is to monitor the purity of the product oxygen produced by the oxygen concentrator. These sensors meet the regulatory requirements for alarming if the oxygen purity drops, but these sensors are typically only used for that purpose, thus they do not give the patient or equipment provider any insight into the operating health of the equipment. The low oxygen alarm is also a reactive alarm since the purity of the oxygen has already fallen below the predetermined minimum level. In the event of a low oxygen alarm trigger, in the best case the patient will be receiving reduced purity oxygen until a backup oxygen source is used or an equipment provider or technician can replace or repair the concentrator. In any case, the low oxygen alarm creates a situation that requires immediate action by the user and/or the equipment provider. This type of fast response is inherently more costly and stressful than a planned maintenance activity. It is the object of this invention to provide means for predicting remaining service life allowing users of appropriately designed concentrators to proactively perform maintenance before the purity of their oxygen has already reached a critical level.

BRIEF SUMMARY OF THE INVENTION

The invention is a portable oxygen concentrator platform, including a PSA/VPSA/VSA system wherein the portable concentrator contains a adsorbent (sieve) bed monitoring system that tracks remaining zeolite useful life and communicates the health status and useful remaining life of the adsorbent beds to the user or equipment provider. The adsorbent bed monitoring system utilizes a variety of measured operating parameters to track the remaining useful life of the product. Such measured operating parameters may include operating pressure, various PSA cycle parameters, oxygen concentration, operating temperature, operating time, and operating frequency. The invention further includes an administrative function that can reset the adsorbent bed monitoring system when the adsorbent beds are replaced. The reset function may also be enabled to reset operating parameters such as cycle frequency, compressor speed, and target pressures to ensure optimal operating efficiency with both new and contaminated sieve beds. The portable concentrator includes all of the concentrator instrumentation, mechanics, and pneumatics and may include a housing; a programmable controller; a user interface; at least one compressor, air control valve, and air filter, a patient delivery apparatus, one or more pressure sensors, one or more temperature sensors, and one or more life clocks. The invention is best applied to the portable medical concentrator field where the concentrator preferably weighs less than 20 pounds, produces less than 55 dba acoustic noise when operating, and has an output gas flow of 5 lpm or less and has rechargeable battery capable of running the concentrator for greater than 0.5 hours. In a preferred embodiment, the concentrator weighs less than about 8 pounds and produces less than 45 dba and a battery life of greater than 2 hours.

For such a portable oxygen concentrator the invention is a method for predicting remaining operating life of the sieve beds including monitoring the oxygen sensor with the controller, and calculating the amount of operating lifetime of the sieve beds remaining using an algorithm executing on the programmable controller. In one embodiment the algorithm is:

$$\text{Remaining \% Life} = 100 - 10(95 - [O_2]);$$

where $[O_2]$ is Oxygen purity.

In an alternative embodiment shown in FIG. 11, the algorithm is:

$$\text{Remaining \% Life} = 100 - 10(95 - [O_2]) - 10(P_{Avg} - P_T) - 2*CFA - 2*CBA - OH/1000 - 1/DC;$$

where;
Oxygen concentration, $[O_2]$
Product Pressure (PSI), $P_p$
Product Pressure (PSI), $P_{Avg}$
Target Product Pressure (PSI), $P_T$
Column Balance (PSI), CB
Column Balance Adjustment, CBA
Cycle Frequency, CF
Cycle Frequency Adjustment, CFA
Operating Hours, OH
Fractional Duty Cycle, DC An alternate version of this algorithm leaves out the $-10(95-[O_2])$ terms and is depicted in FIG. 13.

A further embodiment is shown in FIG. 12. The algorithm is;

$$\text{Remaining \% Life} = 100 - 5(95 - [O_2]) - 5(P_{Avg} - P_T) - 2*CFA - 2*CBA - OH/1000 - 2/DC - (T_o - 35) - (T_s - 25);$$

where;
Oxygen concentration, $[O_2]$
Product Pressure (PSI), $P_p$
Product Pressure (PSI), $P_{Avg}$
Target Product Pressure (PSI), $P_T$
Column Balance (PSI), CB
Column Balance Adjustment, CBA
Cycle Frequency, CF
Cycle Frequency Adjustment, CFA
Operating Hours, OH
Fractional Duty Cycle, DC
Operating Temperature, $T_o$
Storage Temperatures, $T_s$ An alternate version of this algorithm leaves out the $5(95-[O_2])$ terms and is depicted in FIG. 14. In the above embodiments, preferably the invention includes providing a programmable controller generated notification of the remaining operating lifetime. The notification may be by way of at least one of an indicator on the user interface or a wireless notification.

In other embodiments, the method includes replacing the adsorbent beds with new beds or new adsorbent when the remaining operating lifetime reaches a predetermined level. The method may also include running a routine on the programmable controller that resets operating parameters of the concentrator changed to extend operating life back to new adsorber bed compatible settings after the beds are replaced. The operating parameters reset may include at least one of;
PSA/VPSA/VSA Cycle Frequency Adjustment,
Column Balance Adjustment,
valve timing,
compressor speed; and,
clock pointers.

BRIEF DESCRIPTION OF THE DRAWINGS

The understanding of the following detailed description of certain preferred embodiments of the invention will be facilitated by referring to the accompanying figures.

FIG. 10 depicts a simple adsorbent bed life algorithm FIG. 11 depicts an alternative more sophisticated adsorbent bed life algorithm that incorporates additional system information FIG. 12 depicts a second alternative adsorbent bed life algorithm that incorporates additional system information FIG. 13 depicts a third alternative adsorbent bed life algorithm.

FIG. 14 depicts a fourth alternative adsorbent bed life algorithm.

FIG. 15 illustrates the results of the sieve bed adsorbent life algorithms over different variable inputs and compares the outputs from three different possible algorithms.

DETAILED DESCRIPTION OF THE INVENTION

Figure 1:
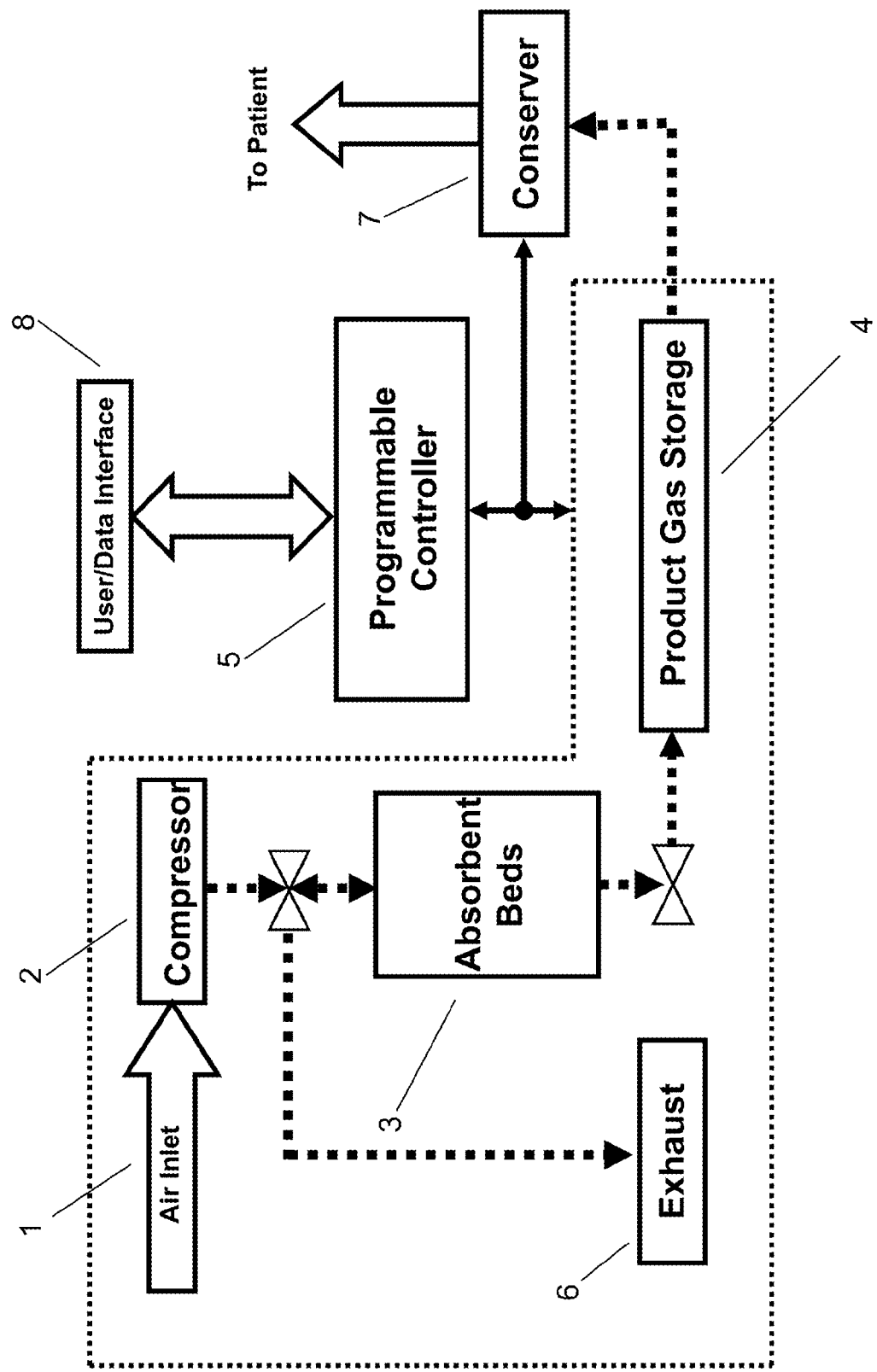
FIG. 1 shows the general elements of gas concentrators as applicable to certain embodiments of the invention.

As described above, one of the main factors limiting concentrator lifetime is moisture contamination of the adsorbent materials in the adsorbent beds.

Despite the effective moisture mitigative measures described in co-pending application Ser. No. 11/998,389 which might remove 40-98% of water molecules from the feed gas stream, some moisture will remain in the beds 3 when the concentrator is turned off. For the case where there is a desiccant layer, even for a very dry design, the desiccant 11 exists to remove any remaining water as well as other impurities, such as $CO_2$, from the feed gas. During operation impurities are largely removed from the concentrator, as the bed 3 is back-purged or evacuated with vacuum periodically in the Adsorption Cycle, thereby not leaving time for moisture and other impurities to diffuse into adsorbent. When the concentrator is not running, particularly for a long period of time, there will be a strong driving force to diffuse for any impurities adsorbed on the pretreatment layer (or feed end of the bed in the case of no pretreatment layer used) or in the gas phase in the void space of the desiccant/adsorbent at the feed end of the bed. If the concentrator is not sealed to the outer atmosphere via a valve on the exhaust contaminants can diffuse either to the outer atmosphere (likewise other contaminants can diffuse into the beds) or the contaminants can diffuse into the active "clean" section of the bed(s). If the concentrator is sealed to the outer atmosphere via a valve, any impurities present will diffuse into the bed only.

Pretreatment layers are often selected due to their ease of regeneration during process cycles relative to that for the contaminants in the active air separation layer. Thus during shutdown conditions the result can be a material with a low affinity for a given contaminant adjacent to a material with a high affinity for a given contaminant, and a large gradient in chemical potential for the contaminant provided sufficient treatment of the feed gas has taken place and the air separation layer has remained impurity-free. Given the complex array of components required to prevent the contamination of zeolite while a portable oxygen concentrator is running and while it is in storage, the inventors have conceived methods to estimate the remaining adsorbent bed life to better plan and execute maintenance requirements on portable concentrators that are in use in the field.

While it is known in the art to monitor the oxygen purity of the product oxygen gas, there have been no portable concentrators that are able to proactively predict the remaining life of the zeolite. Since the life of the zeolite can vary dramatically according to the usage environment, the storage environment, the usage frequency, and the usage flow setting, the service providers and the patients have never had adequate visibility into the service requirements and service intervals of their equipment. The invention herein requires a concentrator to monitor operating parameters of the system and integrate the data streams into algorithms that can predict remaining life of the concentrator.

Figure 8:
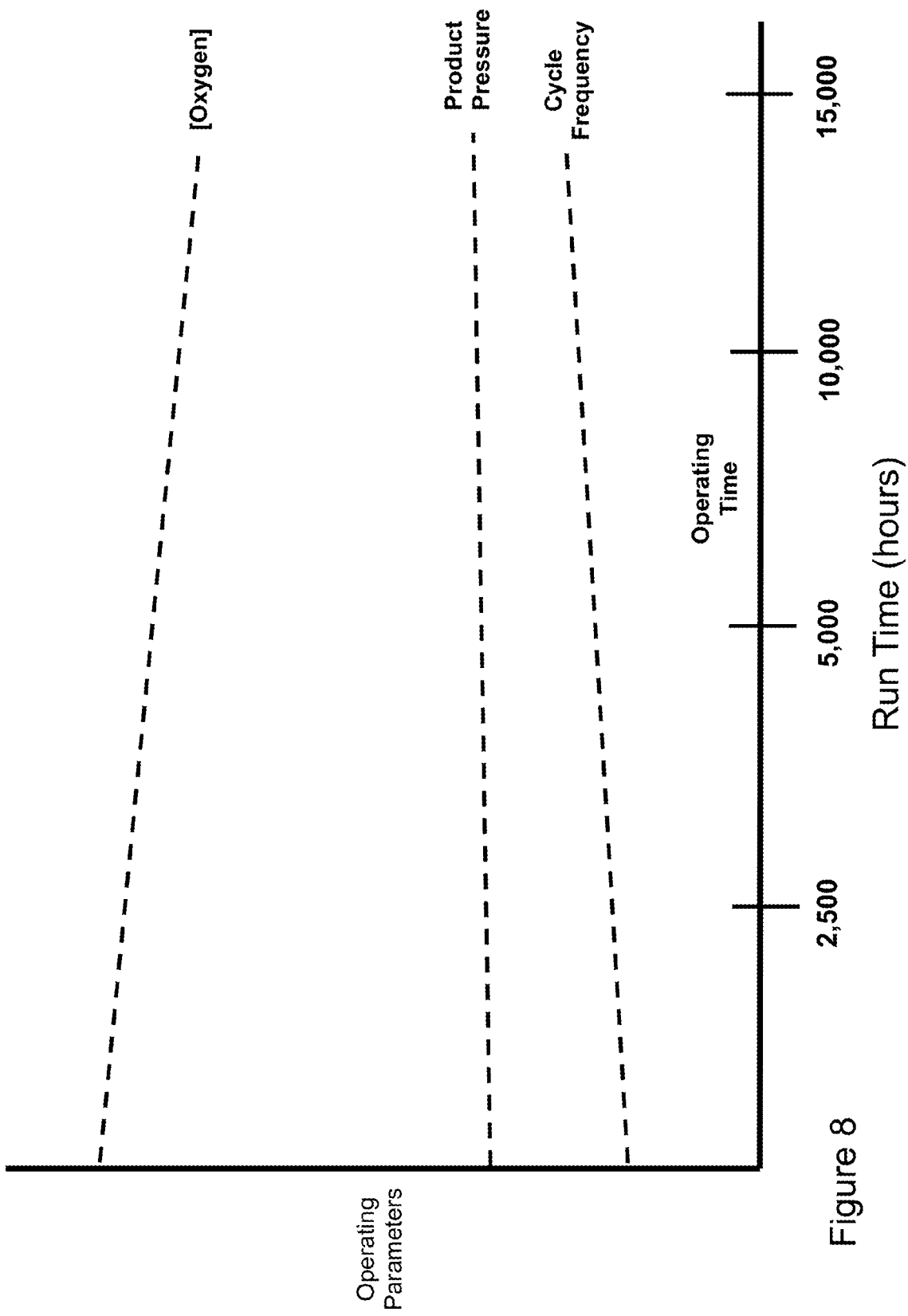
FIG. 8 illustrates how adsorption variables change over time in a running system
Figure 9:
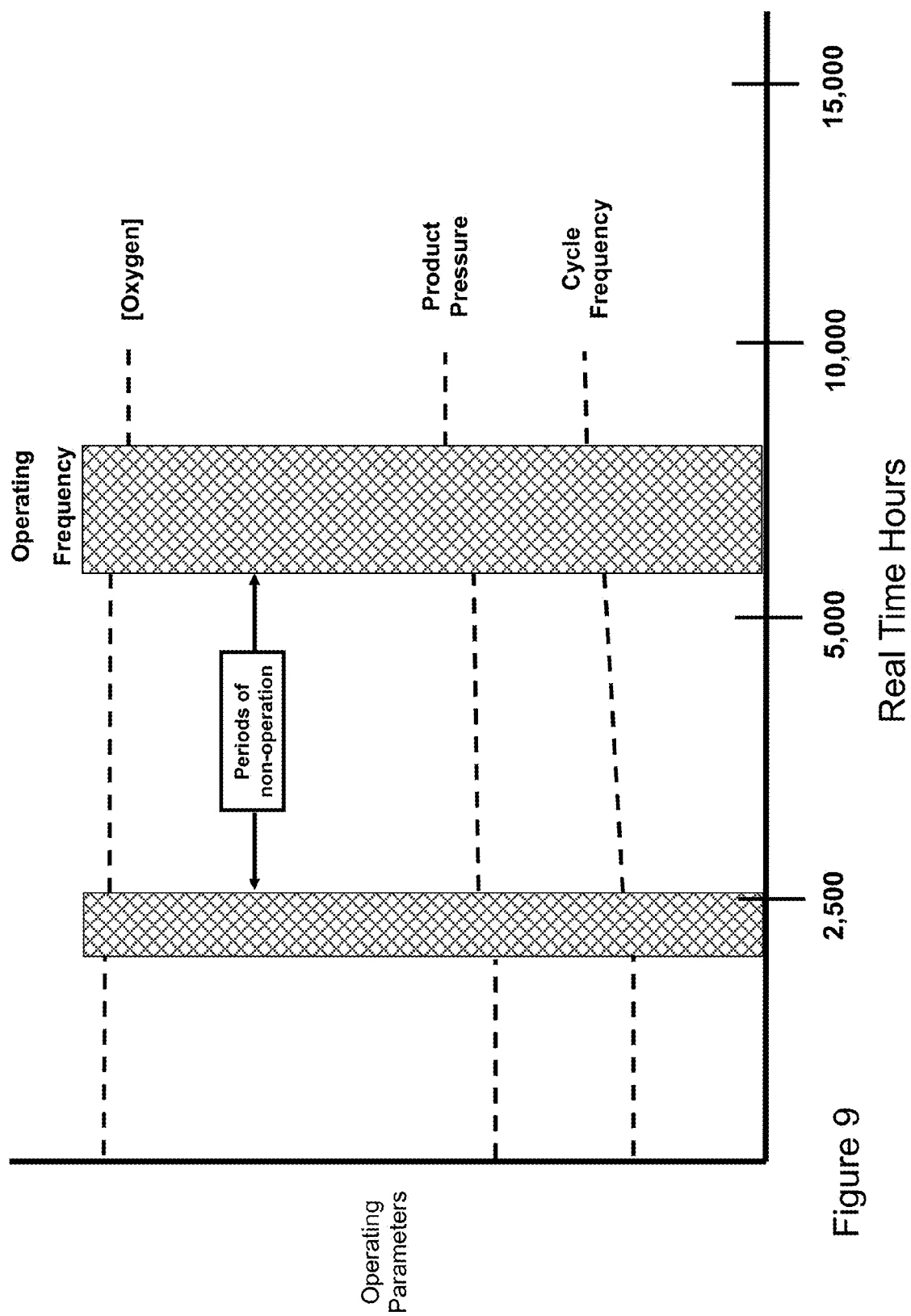
FIG. 9 illustrates how adsorption variables change over time in a system where the device is run intermittently

A particularly effective set of process signals to monitor is the combination of oxygen purity and oxygen product pressure. Moisture and other impurities displace nitrogen in the binding sites of the zeolite, the resulting pressure rise above the Target Product Pressure ($P_T$) and decrease in oxygen purity, as depicted in FIG. 8, may be detected as a sign of decreasing zeolite capacity. The increase in pressure, noted as the difference in $P_T$ and $P_p$ or $P_{avg}$ in FIGS. 10-14, is proportional to the decrease in available capacity in the adsorber bed. Further, the change in oxygen concentration, noted as $[O_2]$ in FIGS. 10-14, may also indicate the severity of the loss of capacity on the performance of the system. Monitoring the change in oxygen concentration over time may yield a rudimentary, but satisfactory adsorbent bed life prediction. Such a simple algorithm would be able to predict the percentage of bed life remaining and therefore provides useful results. The simple algorithm is shown in FIG. 10. However an algorithm based on oxygen purity alone may not be able to predict the amount of time remaining until a service is needed since the output of the algorithm may jump dramatically after periods of inactivity as depicted in FIG. 9, due to moisture or other contaminants diffusing across the beds as described above.

A more advanced system to monitor sieve bed life may include additional parameters that can increase the accuracy of the sieve bed life prediction. By monitoring the Fractional Duty Cycle (DC) and storage temperature ($T_s$) of the concentrator the system may successfully predict the faster zeolite degradation due to diffusion of contaminants throughout the zeolite bed that may occur during storage. If the oxygen concentration, or oxygen concentration ($[O_2]$) and product oxygen pressure ($P_p$ or $P_{avg}$), alone were used for the sieve bed life prediction, the life prediction may change substantially after a period of inactivity of the concentrator. An embedded real time clock can be used to calculate The Operating Hours (OH), and the Fractional Duty Cycle (DC). The Fractional Duty Cycle is simply calculated as the Operating Hours divided by the non Operating Hours. The improvement in accuracy resulting from the additional information provided by the operating hours (OH) and the Fractional Duty Cycle can substantially improve the accuracy of the overall sieve bed life prediction in terms of remaining sieve bed life as well as predicted time remaining until the beds need to be serviced.

The inventors have already disclosed methods to extend the operating life of a concentrator by adjusting PSA cycle parameters. A particular method to extend lifetime by adjusting the bed pressure balance is disclosed in U.S. Pat. No. 7,857,894. In this patent it is disclosed that by measuring the pressure difference between the adsorbent beds, noted as CB in FIGS. 10-13, and adjusting the various valve timings of the valves that control flow through the columns for feed and purge cycles, it is possible to adjust for a certain amount of degradation, particularly due to an imbalance in the bed pressures (CB), without replacing the beds. The extent of valve timing adjustments is termed Column Balance Adjustment or CBA in FIGS. 10-13. Thus, the system may adjust its operating parameters, primarily through valve timing and compressor speed to compensate for contamination of the sieve material so that overall product oxygen concentration, ($[O_2]$), is not impacted. Further, by adjusting the PSA Cycle Frequency (CF) through the Cycle Frequency Adjustment parameter (CFA) to shorten the length of the PSA cycle steps, less air per cycle is processed, and the system may operate with improved oxygen concentration output even with contaminated zeolite. By measuring and adapting to these measured parameters, the oxygen concentration output of the concentrator may remain relatively constant over time even though the capacity and adsorbent beds is decreasing. These parameters either in part or in whole can then be input into the algorithm for predictive sieve bed life remaining so that the bed life can be very accurately tracked and predicted. A more complex algorithm using these parameters is shown in FIG. 11.

Further, the implementation of data logging and temperature monitoring can enable the algorithm to be adjusted for such parameters as operating hours (OH), Fractional Duty Cycle (DC), operating temperature ($T_o$), and storage temperature ($T_s$). All of these parameters impact the estimated life of the zeolite, so incorporating them as inputs to the life estimating algorithm, as seen in FIG. 12, can give improved accuracy and predictive value to the sieve bed monitoring algorithm.

It will be clear to someone skilled in the art that there are numerous possible implementations of the sieve bed monitoring algorithms and that the inclusion or different weighting of various parameters can be used to tune the algorithm for a given portable oxygen concentrator design or usage application. For example, various measured parameters could be removed from the algorithm or alternate algorithms developed using some or all of the measured parameters discussed while still achieving the same goal of predicting bed capacity decrease. This is exemplified in the algorithms displayed in FIGS. 13 and 14, which are examples of modifying the algorithms disclosed in FIGS. 11 and 12, by removing the oxygen concentration term from the algorithm.

It will furthermore be clear to someone skilled in the art that various other environmental conditions such as relative humidity or methods of sensing bed capacity change as a function of time, operating, and storage conditions could be incorporated into these or similar algorithms. These methods include, but are not limited to, breakthrough detection, breakthrough detection relative to expected cycle step time, and blowdown or evacuation volume monitoring. Measurement of these parameters would typically require additional sensors and increase device cost.

FIG. 15 shows the different results obtained from the progressively more detailed algorithms as a function of operating hours. As can be seen in FIG. 15, the more the concentrator sieve beds have been contaminated, the more accuracy is gained by the more advanced algorithms. However, even the simple oxygen purity only algorithm depicted in FIG. 10 is clearly accurate enough to provide an advantage over the traditional low oxygen purity alarm. Results from the $3^{rd}$ and $4^{th}$ Alternative Algorithms are those calculated using those algorithms exhibited in FIGS. 13 and 14, and further demonstrate that useful conclusions can be deduced by using a more limited set of measured parameters from the concentrator. The spirit of the invention is not therefore intended to be limited to the specific algorithms disclosed but rather that of using measured parameters of a portable oxygen concentrator to predict service life of the oxygen separating media. Clearly other algorithms and variations of the exemplary algorithms discussed herein that fall within the scope of the invention will suggest themselves to one skilled in the art.

Whichever algorithm is used, the result is that the information about remaining life can be used to request service before a fault occurs in the concentrator, and that the specific service is typically the replacement of the adsorbent beds, or alternatively the replacement of the adsorbent in the beds. It is possible, as disclosed in application Ser. No. 13/066,716, to design a concentrator with user replaceable beds so that an actual user can perform adsorber replacement without the involvement of a technician or service provider. However, most concentrators still use plumbing and design elements that do not allow an untrained user to perform maintenance on the adsorber beds. By including an adsorber monitoring system in these non-user serviceable concentrators, adsorber replacement can still be performed proactively before a low oxygen failure without removal of the equipment from the point of use. Thus, it is an important part of the invention to notify the user and/or caregiver to either order new beds for the user replaceable scenario or schedule service for other cases.

Figure 2:
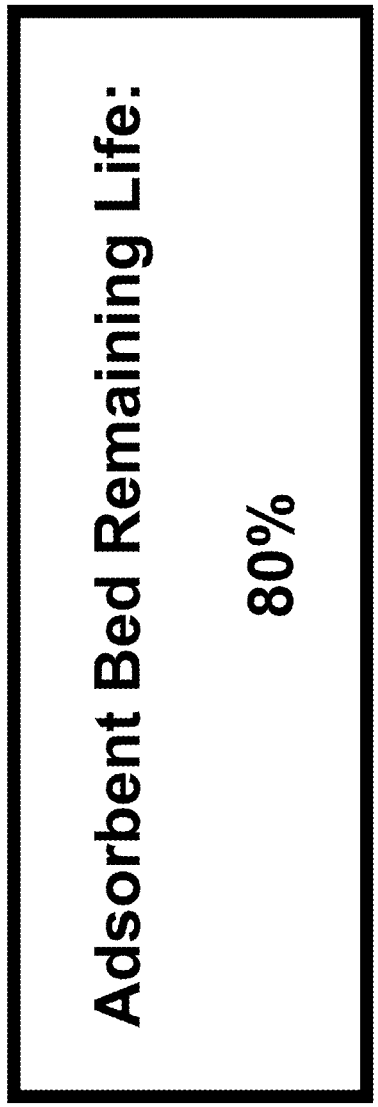
FIG. 2 illustrates a typical LCD message indicating remaining sieve bed life
Figure 3:
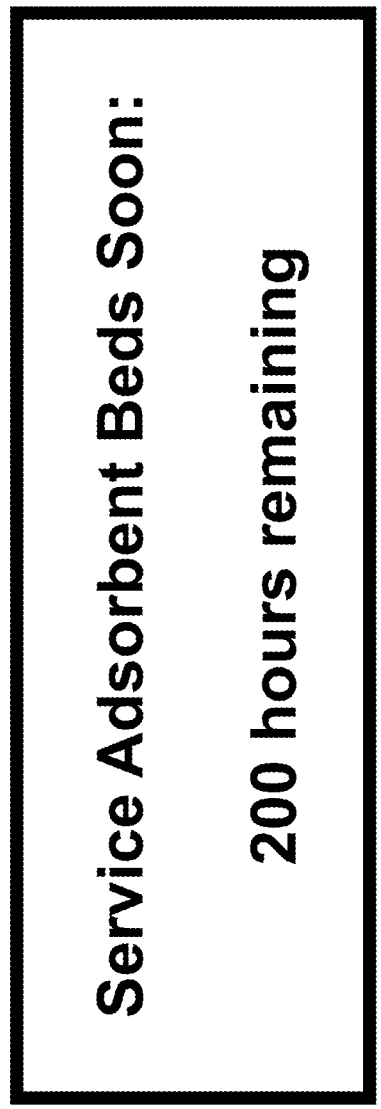
FIG. 3 illustrates a typical LCD message indicating that the sieve beds require service.
Figure 4:
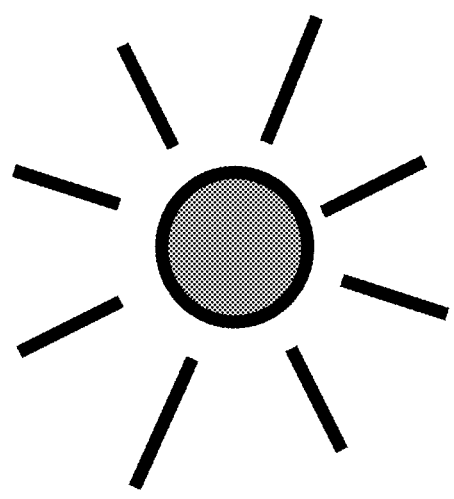
FIG. 4 depicts an LED or audible alert signal that the sieve beds require service
Figure 5:
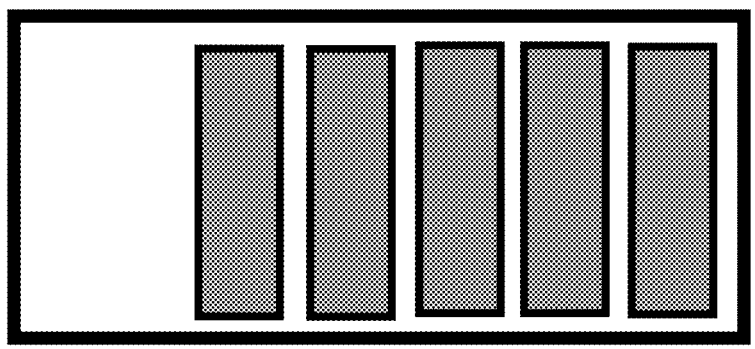
FIG. 5 depicts one example of a remaining sieve bed life indicator
Figure 6:
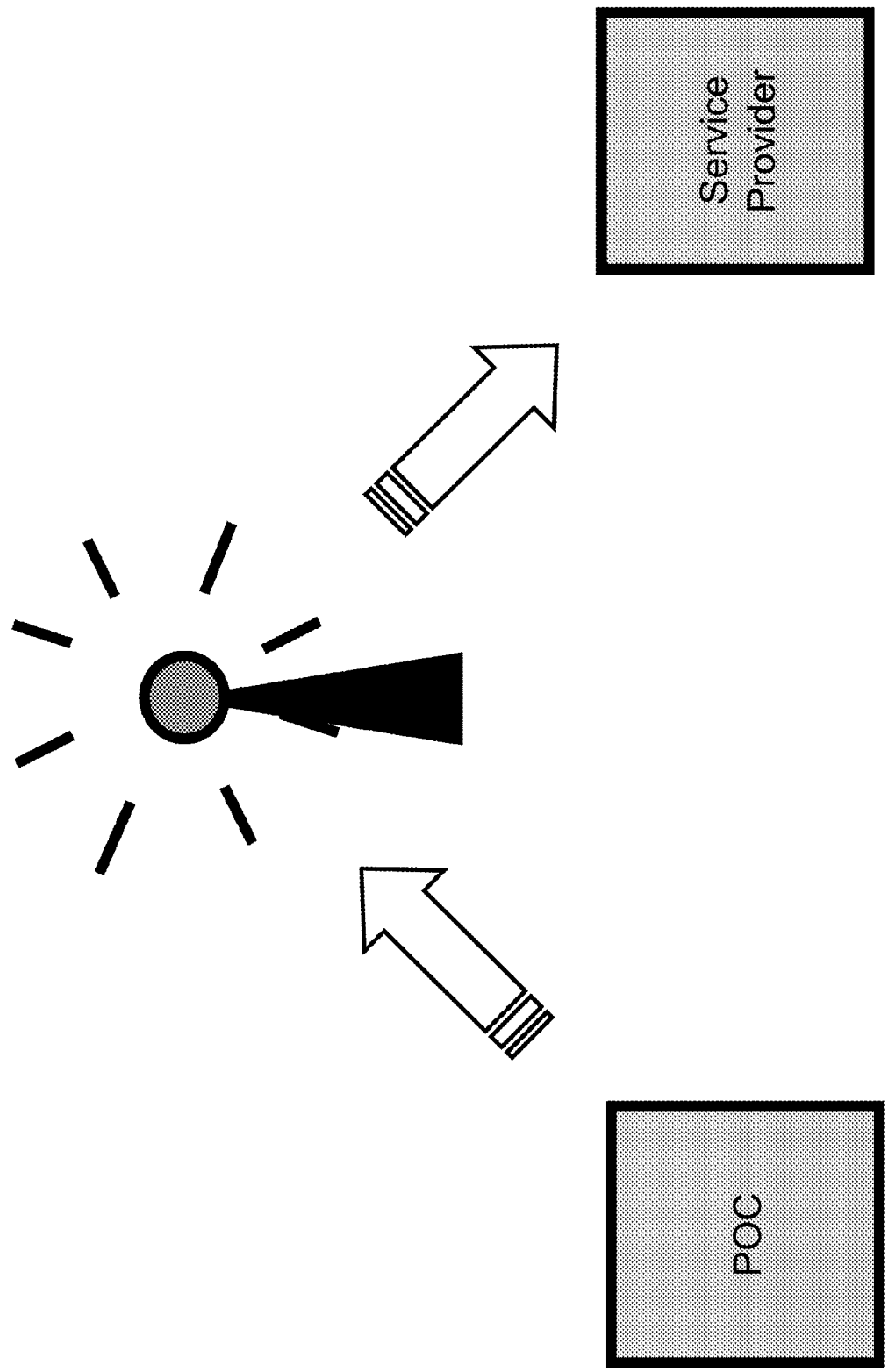
FIG. 6 depicts a service signal that may be sent from the concentrator to a service provider to report remaining sieve bed life or to report a need for sieve bed service.

A variety of ways to perform this notification will suggest themselves to one skilled in the art. FIG. 2 shows a message on the user interface indicating remaining life. When the life gets to a predetermined level the use should take action. FIG. 3 illustrate a display specifically instructing the user to take action. FIG. 4 shows a visual or audio direct indicator such as a blinking light or audio alarm. FIG. 5 is an alternative display. FIG. 6 illustrates a scenario where the concentrator has a link, such as a cell modem to the service provider or caregiver. In such a case the concentrator controller can notify someone directly that the concentrator needs to have the beds replaced.

Figure 7:
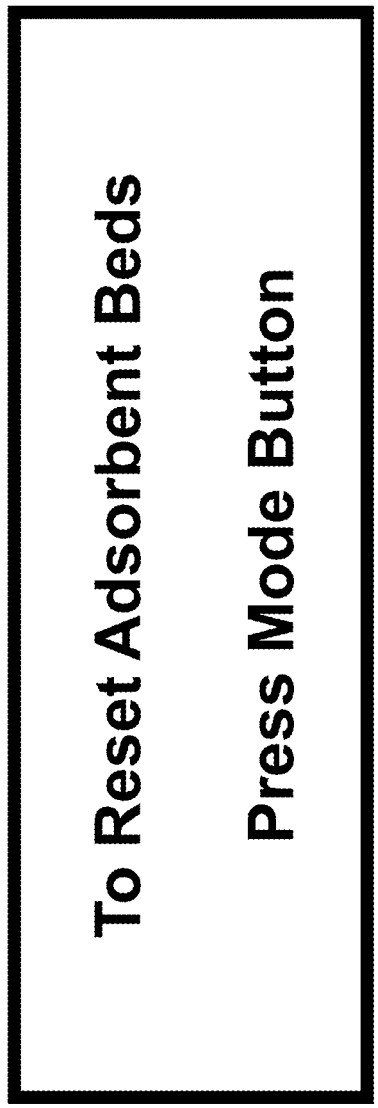
FIG. 7 depicts the display during reset of the sieve bed monitoring routine.

Once the beds are replaced, if the concentrator has been configured to adjust operating parameters to extend life, as described above, then, the system then needs to be reset to again optimally operate on the new sieve beds with the originally designed capacity restored. Since such an operation is beyond the capability of the user or low level field technician, the controller preferably also has a reset routine to acknowledge the installation of new adsorbent beds, reset the clock pointers, clear any notifications that the sieve beds need to be serviced, and reset the operational parameters such as compressor speed and valve timing. The reset function may be carried out by a series of user executed button commands in response to an appropriate LCD message such as the one shown in FIG. 7, or the concentrator could automatically adapt to the new adsorbers by detecting the changed operating parameters such as operating pressure or oxygen concentration.

We claim:
1. For a portable oxygen concentrator including a PSA/VPSA/VSA system with adsorbent beds, a programmable controller, a user interface, at least one of a pressure or an oxygen purity sensor for measuring data on operating parameters of the concentrator, and at least one time measuring device for measuring at least one of operating and non-operating times of the concentrator; a method for predicting remaining operating life comprising;
   acquiring data from at least one operating sensor with the controller for a time period encompassing a plurality of operating and storage time periods as determined by the controller and the time measuring device; and,
   executing an algorithm on the controller for predicting the amount of usable bed lifetime remaining using a combination of the operating data and the time data;
   wherein the concentrator has an output gas flow of 10 lpm or less.
2. The method of claim 1 wherein the concentrator has a gas output flow of 5 lpm or less.
3. The method of claim 1 wherein the concentrator weighs less than 20 pounds.
4. The method of claim 1 wherein the concentrator produces less than 55 dba acoustic noise when operating.
5. The method of claim 1 wherein the concentrator has a rechargeable battery capable of running the concentrator for greater than 0.5 hours.
6. The method of claim 1 wherein the sensor data includes at least one of;
   product oxygen concentration,
   product gas pressure,
   adsorbent bed pressure.
7. The method of claim 1 wherein the time data is at least one of real time clock data and hour meter data.

* * * * *